(12) United States Patent
Park

(10) Patent No.: US 6,916,065 B2
(45) Date of Patent: Jul. 12, 2005

(54) ROTATING PATIENT CHAIR WITH EAR DIAGNOSIS AND TREATMENT UNIT

(76) Inventor: Ja-Ryoung Park, 10-1003, Woosung Apt., Seocho 1-Dong, Seocho-Gu, Seoul (KR)

(*) Notice: Subject to any disclaimer, the term of this patent is extended or adjusted under 35 U.S.C. 154(b) by 257 days.

(21) Appl. No.: 10/212,299

(22) Filed: Aug. 2, 2002

(65) Prior Publication Data

US 2003/0042772 A1 Mar. 6, 2003

(30) Foreign Application Priority Data

Aug. 28, 2001 (KR) .......................................... 2001-52021
Mar. 26, 2002 (KR) .......................................... 2002-16272
Apr. 26, 2002 (KR) .......................................... 2002-22906

(51) Int. Cl.[7] .......................... A61G 15/02; A47C 7/72; A47C 1/06; A47B 83/02
(52) U.S. Cl. .............................. 297/217.1; 297/217.3; 297/217.4; 297/217.6; 297/330; 297/344.21; 297/344.22; 297/344.23; 297/344.26; 297/135; 297/152; 297/153; 297/154; 297/155; 297/170; 297/172
(58) Field of Search .............................. 297/330, 217.1, 297/217.3, 217.4, 344.21, 344.22, 344.23, 344.26, 135, 152, 153, 154, 155, 170, 217.6, 172

(56) References Cited

U.S. PATENT DOCUMENTS

| | | | | |
|---|---|---|---|---|
| 336,220 A | * | 2/1886 | Farrar ................ | 297/344.21 X |
| 2,148,347 A | * | 2/1939 | Gray .................... | 297/217.4 X |
| 2,416,410 A | * | 2/1947 | Shampaine ............. | 297/330 X |
| 2,440,644 A | * | 4/1948 | Powell ............... | 297/344.26 X |
| 3,135,550 A | * | 6/1964 | Bosack ............... | 297/344.22 X |
| 3,172,699 A | * | 3/1965 | Naughton ............... | 297/330 X |
| 3,311,411 A | * | 3/1967 | Page et al. .................. | 297/170 |
| 3,368,845 A | * | 2/1968 | Teruo .......................... | 297/330 |
| 3,386,766 A | * | 6/1968 | Gorelick ................. | 297/330 X |
| 3,514,153 A | * | 5/1970 | Ferguson et al. ....... | 297/330 X |
| 4,097,016 A | * | 6/1978 | Petrucci ............. | 297/344.26 X |
| 4,500,134 A | * | 2/1985 | Kaneko et al. ............. | 297/170 |
| 4,600,239 A | * | 7/1986 | Gerstein et al. ....... | 297/344.23 |
| 4,913,264 A | * | 4/1990 | Voves et al. ........ | 297/344.26 X |
| 4,929,023 A | * | 5/1990 | Rasmussen ................. | 297/330 |
| 5,601,331 A | * | 2/1997 | Austin et al. ............... | 297/170 |
| 5,720,462 A | * | 2/1998 | Brodersen .......... | 297/344.21 X |
| 5,733,006 A | * | 3/1998 | Woods ................... | 297/344.22 |
| 5,803,547 A | * | 9/1998 | Brown .................. | 297/344.23 |
| 5,884,350 A | * | 3/1999 | Kurze .................... | 297/330 X |
| 2004/0007907 A1 | * | 1/2004 | DiRe ....................... | 297/217.3 |

FOREIGN PATENT DOCUMENTS

| EP | 584439 A1 | * | 3/1994 | .............. 297/217.3 |
|---|---|---|---|---|
| KR | 20-0247914 | | 7/2000 | |

* cited by examiner

*Primary Examiner*—Rodney B. White
(74) *Attorney, Agent, or Firm*—Gordon & Rees LLP

(57) ABSTRACT

The present invention relates to a rotating patient chair mounted with an integrated ear diagnosis and treatment unit that controls the position of a microscope 48 and a monitor 50 rotating around the rotating patient chair 30 at a predetermined angle or 180 degrees, the unit including: suctioners 44, 52, a treatment board 46, a blood pressure tester 54 and a manipulating switch box 40 for controlling the diagnosis and treatment tools, and the monitor 50 and the microscope 48 positioned in correspondence with the patient's ears anatomically positioned at 180 degrees to enable the patient to observe all of the treatment processes to the ear parts including the thin, dark auditory canals and eardrums on the monitor 50 installed at an opposite side and to enable the practitioner to explain all of the treatment processes shown on the monitor to the patient and his guardians, thereby improving reliability on the practitioner and the treatment processes and maximizing the treatment effects, and performing diagnosis and treatment processes to the patient's ears by not letting the practitioner or patient move around but merely by rotating the ear diagnosis and treatment unit, minimizing discomfort and inconvenience to the practitioner or patient, shortening the medical treatment time and minimizing the space of a treatment room occupied by the diagnosis and treatment unit.

5 Claims, 15 Drawing Sheets

US 6,916,065 B2

ROTATING PATIENT CHAIR WITH EAR DIAGNOSIS AND TREATMENT UNIT

FIELD OF THE INVENTION

The present invention relates to a rotating patient chair mounted with an ear diagnosis and treatment unit, and more particularly, to a rotating patient chair mounted with an ear diagnosis and treatment unit including a variety of diagnosis and treatment tools to treat ears at an otorhinolaryngology department, for instance, suctioners, a treatment board, a microscope with a CCD (charge coupled device) camera, a monitor (image display on which a patient can observe a whole treatment process), a manipulating switch box and the like.

BACKGROUND OF THE INVENTION

A general treatment unit used at an otorhinolaryngology department has been disclosed at Korean Utility Model No. 247914. As shown in FIGS. 1 and 2, the general treatment unit 17 includes a suctioner 1, microscope with a CCD camera 3, patient monitor 5, practitioner monitor 7, stand 9, film view box 11, light source 13 and manipulating switch box 15. The treatment unit body 17 is fixedly arranged at a position, in a predetermined distance, away from both the practitioner chair 20 and a plurality of rotating patient chairs 22, so that the practitioner can medically treat patients respectively seated at rotating patient seats 22 by using the treatment tools distributed and mounted at predetermined positions of the unit body 17.

However, since the general unit body 17 thus constructed is fixedly arranged at a position in a predetermined distance away from the rotating patient chair 22, there have been problems in that the practitioner frequently has to move the treatment tools of the unit body 17 to the rotating patient chairs 22 for each treatment and much space of a diagnosis room is occupied by the treatment unit body 17.

Particularly, the microscope 3 and monitor 5 are installed on the unit body 17 regardless of the rotational direction of the rotating patient chair 22 or the position of both ears of the patient, anatomically positioned apart at 180 degrees of the human body. When treatment is performed on a patient seated on the designated rotating patient chair 22 without letting the patient move, while both of his or her left and right ears are checked through the patient monitor 5, there has been a problem of inconvenience in that it is necessary for the practitioner to move around to the patient's ears and make adjustments in the positioning of the microscope 3 after the patient's face or the rotational movement of the rotating patient chair 22 is stopped to align the sight of the patient sitting on the rotating patient chair 22 with the angle of the patient monitor 5.

If a practitioner treats a patient's ears through the microscope 3 while being seated on the practitioner's chair 20, there are methods of treating the ear by moving the patient to a plurality of rotating patient chairs 22 or by the patient remaining in one seat and rotating one designated rotating patient chair 22.

In one method, the patient is treated on both the right and left rotating patient chairs 22 so that the patient's sight can be conveniently aligned with the patient's monitor 5. There is an advantage in that the patient can observe all of the treatment processes of both ears on the patient monitor 5. However, there is a problem in that the patient must inconveniently move back and forth from chair to chair, causing the treatment process to take a longer time.

In another method, a patient is treated while being seated on one rotating patient chair 22 without the inconvenience of moving back and forth between the plurality of rotating patient chairs 22 for medical treatment. However, since the patient's sight and the patient monitor 5 become disaligned, the patient can only see the treatment process of one ear on the patient monitor 5.

SUMMARY OF THE INVENTION

It is an object of the present invention to provide a rotating patient chair mounted with an integrated ear diagnosis and treatment unit (for instance, monitor, microscope, treatment board, suctioner, blood pressure tester, etc.) by which diagnosis and treatment can be performed on both ears without letting the practitioner or patient move around but by merely rotating the ear diagnosis and treatment unit, thereby minimizing inconvenience to the practitioner or patient, shortening the time of medical treatment and minimizing the space of a room occupied by the diagnosis and treatment unit.

It is another object of the present invention to provide a rotating patient chair mounted with an integrated ear diagnosis and treatment unit in which the monitor and microscope can simultaneously be rotated in a circle around the rotating patient chair in relation to both of the patient's ears, enabling the patient to observe all of the treatment process to his or her ears, including the thin, dark auditory canals and eardrums, on the monitor installed on the opposite side. This configuration also enables the practitioner to explain all of the treatment process shown on the monitor to the patient and his guardian, thereby improving reliability on the treatment processes and maximizing the effects of the treatment.

In order to accomplish the aforementioned objects of the present invention, there is provided a rotating patient chair mounted with an ear diagnosis and treatment unit, wherein the ear diagnosis and treatment unit includes a suctioner, a treatment board, a microscope having a CCD camera, a monitor, and the rotating patient chair includes a seat, a back rest, an arm rest, a chair rotating drive part, the chair comprising:

a manipulating switch box mounted at one side of the chair rotating drive part to control the power of the suctioner, the microscope and the monitor;

a first link mechanism connecting the suctioner, on which the treatment board is mounted, to the back rest to control the horizontal position of the suctioner;

a second link mechanism connecting the microscope to the back rest to control the horizontal and vertical position of the microscope; and a third link mechanism connecting the monitor to the arm rest to control the horizontal position of the monitor.

Also, in accordance with the present invention, there is provided a rotating patient chair mounted with an ear diagnosis and treatment unit, wherein the ear diagnosis and treatment unit includes suctioners, a treatment board, a microscope having a CCD camera, a monitor, and the rotating patient chair includes a seat, a back rest, an arm rest, a chair rotating drive part, the chair comprising:

a first link mechanism connected with the treatment board;

a second link mechanism connected with the microscope;

a third link mechanism connected with the monitor; and a rotational supporting means that connects a rotational axle of the chair rotating drive part to the first, second and third link mechanisms and rotates around the rotational axle of the rotating patient chair to simultaneously or respectively control the position of the microscope and the monitor kept at a predetermined angle.

BRIEF DESCRIPTION OF THE DRAWINGS

Objects and aspects of the invention will become apparent from the following descriptions of preferred embodiments with reference to the accompanying drawings in which:

FIGS. 4 through 7 illustrate a monitor and a microscope which are maintained at 180 degrees against the rotational supporting means in accordance with the second embodiment of the present invention for simultaneous rotation around the patient rotation chair; where FIG. 4 is a perspective view for illustrating the rotating patient chair with an ear diagnosis and treatment unit; FIG. 5 is a front view for illustrating the rotating patient chair with an ear diagnosis and treatment unit.

FIGS. 9a through 10 illustrate a monitor and microscope installed at the rotational supporting means and respectively rotated around the rotating patient chair in accordance with the fourth embodiment of the present invention; where FIGS. 9a and 9b are cross-sectional views for illustrating respective states of the rotational supporting means before and after the operation;

FIG. 10 is a plan for illustrating states of the monitor and microscope that can be respectively rotated around a rotating patient chair while being maintained at a predetermined angle of a degrees;

FIG. 11 is a front view for illustrating the rotating patient chair with an ear diagnosis and treatment unit being mounted thereon; and FIG. 12 is a plan for illustrating the state of the monitor and microscope simultaneously rotated around the rotating patient chair while being maintained at 180 degrees.

DETAILED DESCRIPTION OF THE INVENTION

Figure 1:
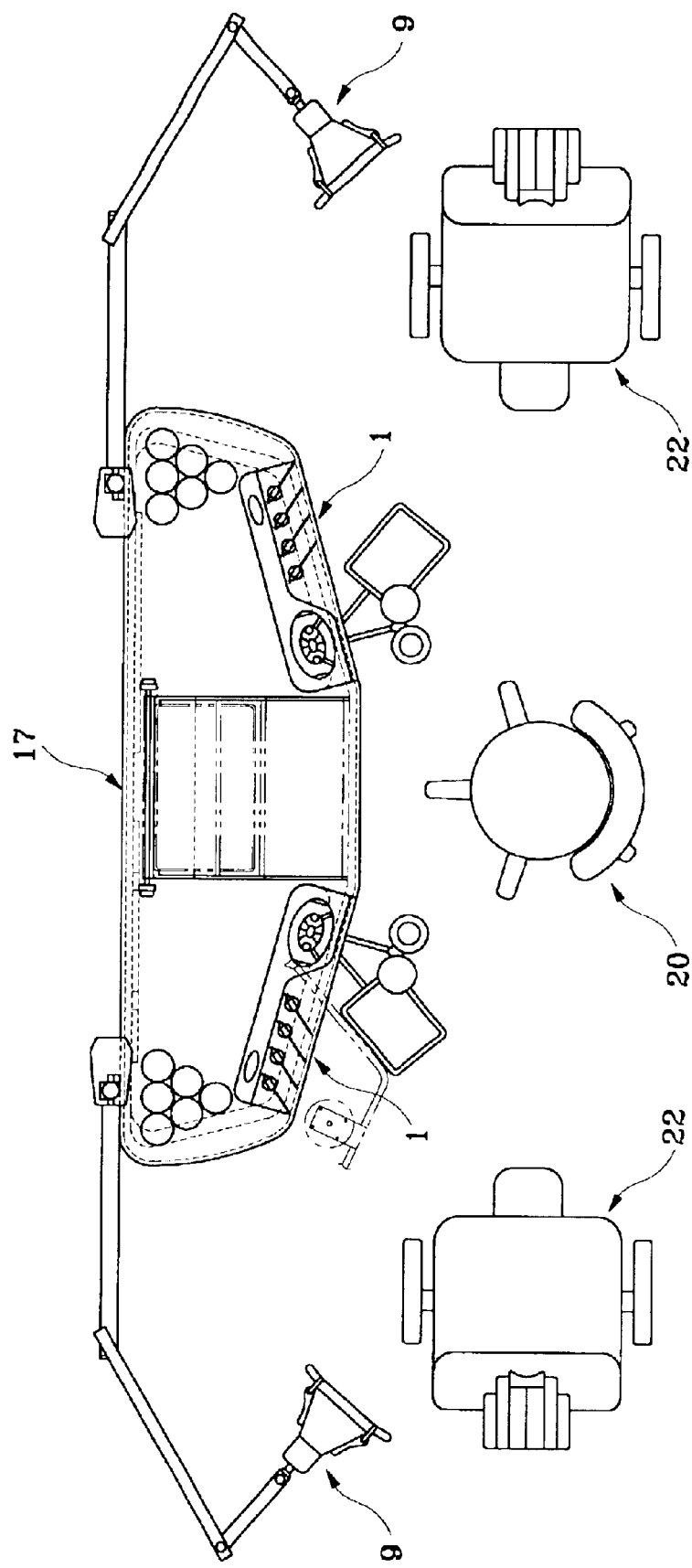
FIG. 1 is a plan view for illustrating the otorhinolaryngological treatment unit of the prior art.
Figure 2:
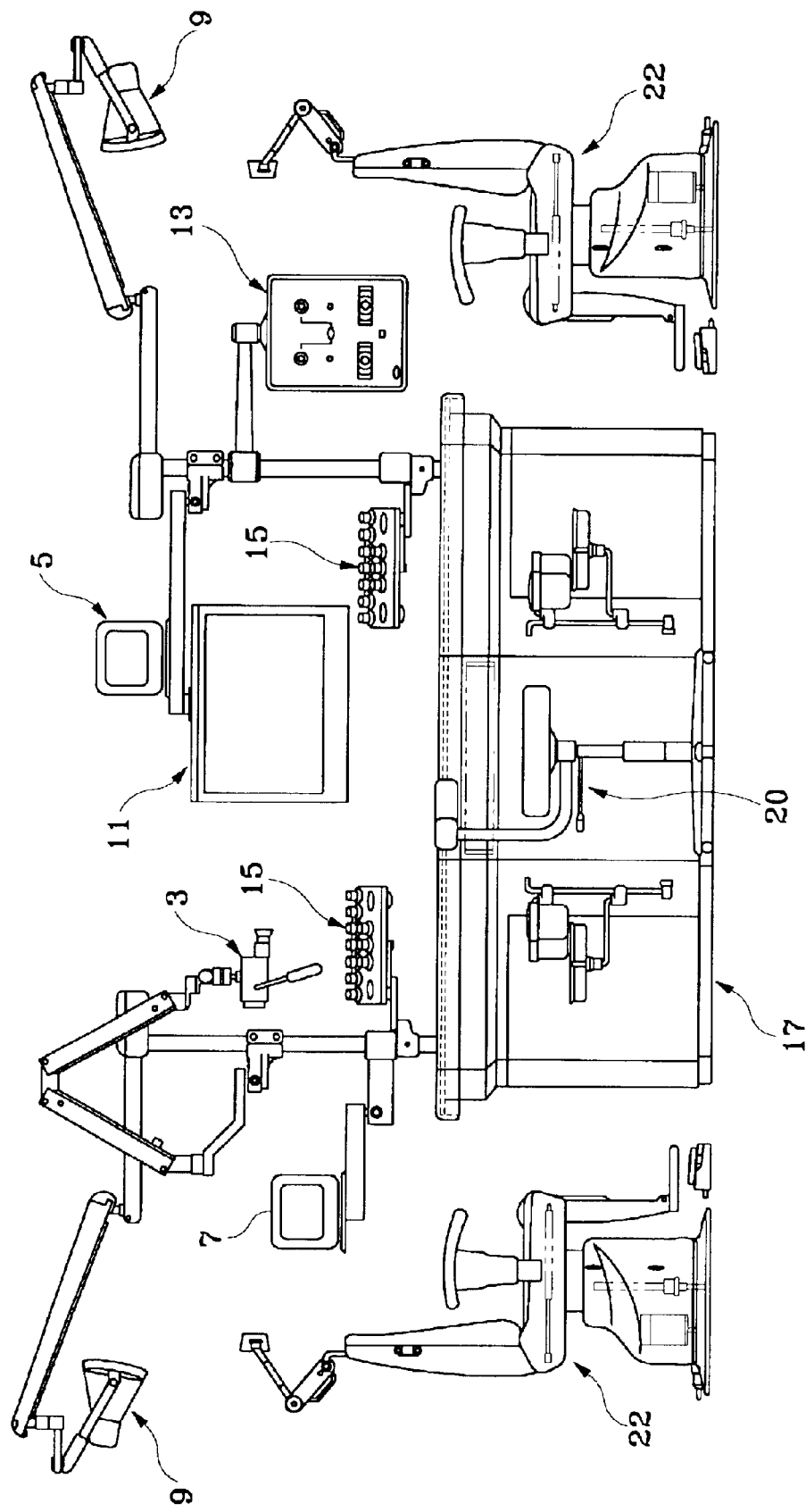
FIG. 2 is a front view for illustrating the otorhinolaryngological treatment unit of the prior art.
Figure 3:
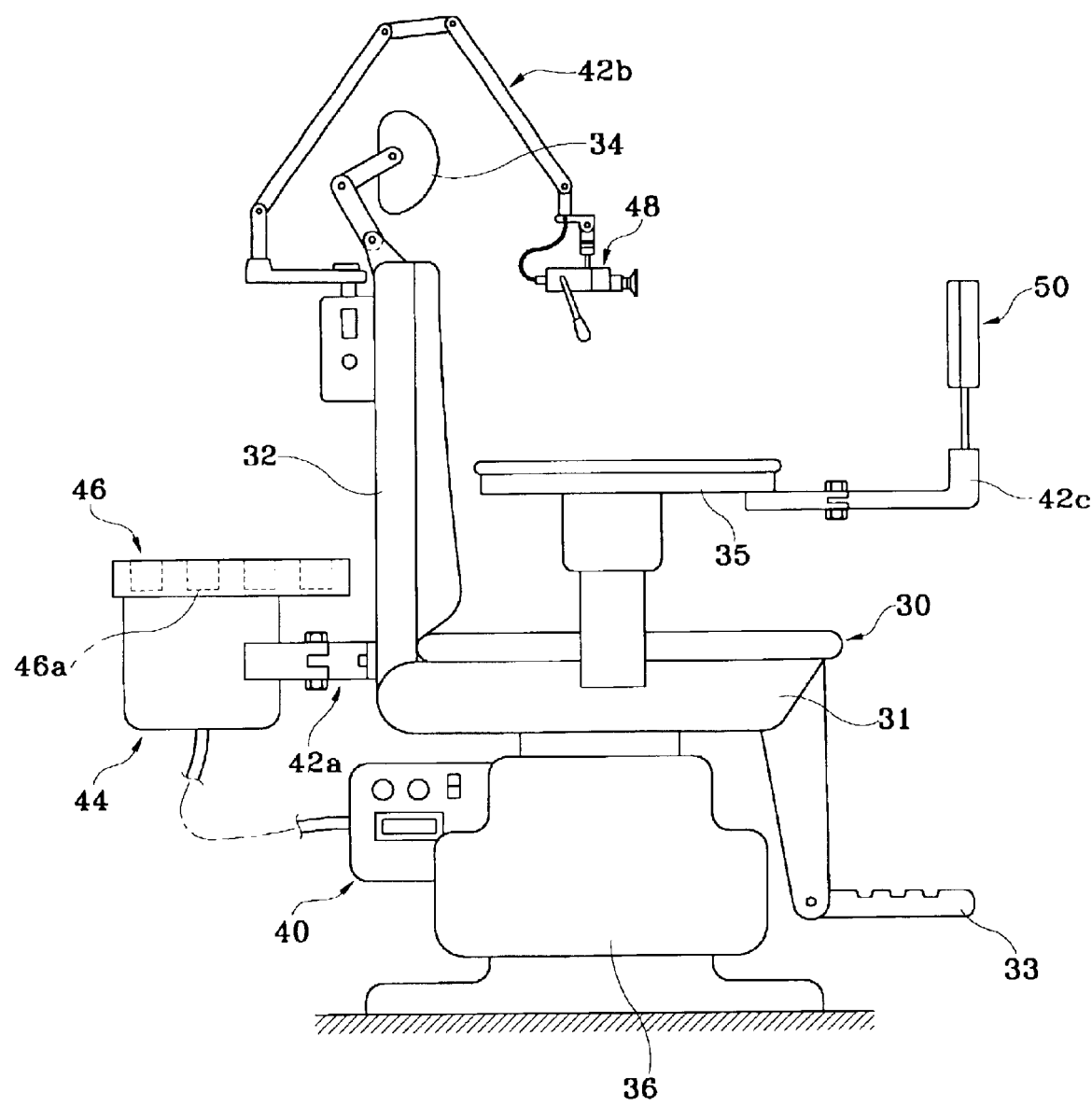
FIG. 3 is a lateral view for illustrating the rotating patient chair with an ear diagnosis and treatment unit in accordance with the first embodiment of the present invention.

Hereinafter, the first embodiment of the present invention will be described with reference to FIG. 3.

In the first embodiment of the present invention, the rotating patient chair 30 includes a seat 31, back rest 32, foot pad 33, head rest 34, arm rest 35, and chair rotating drive part 36. A manipulating switch box 40 is mounted on the back of the chair rotating drive part 36, and a suctioner 44 is mounted on the lower end side of the back rest 32 by a first link mechanism 42a to horizontally control the position of the suctioner 44 in convenience. A board 46 is installed on the upper portion of the suctioner 44 with a plurality of accommodating holes 46a to display treatment products (medical products and treatment tools, etc.).

A microscope 48 having a CCD camera is installed on the upper rear end of the back rest 32 by a second link mechanism 42b to horizontally or vertically control the position of the microscope 48, and a monitor 50 is mounted on the front portion of the arm rest 35 by a third link mechanism 42c to horizontally control the position of the monitor 50.

The manipulating switch box 40 is connected to control the suctioner 44, microscope 48 and monitor 50. The microscope 48 and monitor 50 are connected to a light source using an optical cable.

The first link mechanism 42a has a plurality of split ends connected with a hinge pin (its reference numeral is not shown here) for horizontal folding. Both ends of the first link mechanism 42a are respectively fixed at the lower rear center of the back rest 32 and at the lateral side of the suctioner 44.

The second link mechanism 42b has a plurality of split ends connected with a hinge pin (its reference numeral is not shown here) for vertical folding. Both ends of the second link mechanism 42b are respectively fixed at the upper rear center of the back rest 32 and at the upper portion of the microscope 48 for horizontal rotation.

The third link mechanism 42c has a plurality of split ends connected with a hinge pin (its reference numeral is not shown here) for horizontal folding. One end of the third link mechanism 42c is fixed at the lower front portion of the arm rest 35, and the other end thereof is fixed at the lower center of the monitor 50 for horizontal rotation.

Hereinafter, the operations and effects of the first embodiment of the present invention thus constructed will be described below.

When a patient sits on the rotating patient chair 30 for treatment of his or her ear, the practitioner moves to a predetermined position to conveniently use the microscope 48, suctioner 44 and treatment board 46 mounted on the back rest 32 while sitting on the practitioner chair (not shown here). The patient can observe all of the treatment processes to both ears on the horizontally moving and rotating monitor 50 mounted on the arm rest 35 while sitting on the rotating patient chair 30.

In other words, the microscope 48, suctioner 44, treatment board 46 and monitor 50 are respectively mounted via the first, second and third link mechanism 42a, 42b, 42c for horizontal movement and rotation, so that the practitioner can manipulate the treatment unit and perform treatments without having to move around in the restricted space of a room, reducing the period of treatment time while adding convenience to the treatment process.

When the microscope 48 is positioned close to a patient's ear for treatment, the internal part of a patient's ear is photographed with the CCD camera and transmitted to the monitor 50 to enable the patient sitting on the rotating patient chair 30 and patient's guardians not only to carefully observe all of the practitioner's treatment processes but also listen to the practitioner's explanations, thereby improving reliability on the effects of treatment.

In addition, the microscope 48, suctioner 44, treatment board 46 and monitor 50 are mounted on the rotating patient chair 30 to reduce treatment time, minimize the space of a room occupied by the treatment units, prevent loss or damage of treatment tools and improve comfort and convenience to the patient and practitioner.

The second embodiment of the present invention will be described with reference to FIGS. 4 through 7c.

By way of reference, in the second embodiment of the present invention, identical designations and numerals will be used for indication of the same or equivalent parts as the first embodiment for simplicity of illustration and explanation, detailed descriptions of which will be omitted.

In the ear diagnosis and treatment unit with the rotating patient chair 30 having a seat 31, back rest 32, foot pad 33, head rest 34, arm rest 35 and chair rotating drive part 36 constructed in accordance with the second embodiment of the present invention, a plurality of suctioners 52 are attachably and detachably mounted at left and right ends of the upper portion of the back rest 32; a manipulating box 40 is mounted on the lateral side of the back rest 32; and a cylindrical blood pressure tester 54 is mounted on the upper portion of the arm rest 35 to measure the patient's blood pressure, whereby an arm band is wrapped around the patient's arm and is inflated with air, putting pressure on the arm and later deflated by slowly releasing the air.

The monitor 50 is mounted at a rotational supporting means 60 via a third link mechanism 42c while the microscope 48 is mounted at the rotational supporting means 60 via a second link mechanism 42b. The rotational supporting means 60 is mounted on the external periphery of a rotational axle 36a of the chair rotating drive part 36. Both the monitor 50 and microscope 48 are supported by the rotational supporting means 60 so that the monitor 50 is opposite from the microscope 48 at 180 degrees. The rotational supporting means 60 can simultaneously rotate or stop the monitor 50 and microscope 48 in a circle around the rotating patient chair 30.

The rotational supporting means 60 includes a rotational plate 72, a push lever 80, an elastic member 82, hollow connecting bars 90a, 90b, a first and second fixing bar 92a, 92b, and a first and second moving bar 98a, 98b.

The rotational plate 72 is supported via a bearing 70a at the outer circumferential surface of the rotational axle 36a for free rotation separate from the rotation of the rotational axle 36a and circumferentially formed on the upper surface thereof with a plurality of split grooves 72a each spaced in a predetermined gap thereamong.

The push lever 80 is hinged via a hinge axle 78 in an open hole 74a formed at one side of a case 74 of the chair rotating drive part 36 for horizontal see-saw movement to enable a locking part 80a at one end thereof to be selectively coupled to or separated from one of the plurality of split grooves 72a in the case 74 while the other end thereof is protruded outside of the case 74.

The elastic member 82 is mounted between one side of the case 74 and one end side of the push lever 80 to press one end of the push lever 80. The hollow connecting bars 90a, 90b is fixed at one end thereof on the outer circumferential surface of the rotational plate 72 to face each other at 180 degrees.

The first fixing bar 92a is bent in the shape of an "L" figure and inserted into the connecting bar 90a at one end thereof to horizontally slide without revolving in relation to the corresponding connecting bar 90a. The first moving bar 98a is mounted at an upper circumferential end of the first fixing bar 92a for vertical movement and to support the monitor 50 with the third link mechanism 42c at a predetermined height level. The second fixing bar 92b is bent in the shape of an "L" figure with one end thereof inserted into the connecting bar 90b to horizontally slide without revolving in relation to the corresponding connecting bar 90b and supports the treatment board 46 with the first link mechanism at a predetermined height level. The second moving bar 98b is mounted at an upper circumferential end of the second fixing bar 92b for vertical movement and supports the microscope 48 with the second link mechanism 42b at a predetermined height level.

The first link mechanism 42a has a plurality of split ends connected with a hinge pin (its reference numeral is not shown here) for horizontal folding, with one end thereof mounted around the outer circumferential surface of the fixing bar 92b for horizontal rotation and the other end thereof fixed at the lower central surface of the treatment board 46.

The second link mechanism 42b has a plurality of split ends connected with hinge pins (reference numerals not shown) for vertical folding, with one end thereof fixed at the upper circumferential surface of the moving bar 98b for horizontal rotation and the other end thereof fixed at the upper surface of the microscope 48 for horizontal rotation.

The third link mechanism 42c has a plurality of split ends connected with hinge pins (reference numerals not shown) for horizontal folding, with one end thereof fixed at the outer circumferential surface of the moving bar 98a for horizontal rotation and the other end fixed at the lower central surface of the monitor 50 for horizontal rotation.

The rotational plate 72 is formed in a ring shape and mounted via a bearing 70a inserted between the internal circumferential surface thereof and the outer circumferential surface of the rotational axle 36a. A second bearing 70b is inserted between the lower surface of the rotational plate 72 and the upper portion of a base plate 100 rotatably supporting the lower end of the rotational axle 36a.

The case 74 is mounted on the outer circumferential surface of the rotational axle 36a via a third bearing 70c not to be in contact with the upper surface of the rotational plate 72 at the lower surface thereof. An open hole 74a is formed at one lateral side of the case 74 for inserting the push lever 80 therein. Also, a horizontally positioned fixing piece 74b is integrated at the upper internal surface of the open hole 74a.

A plurality of hinge pieces 76 are vertically and integrally fixed at the lower central surface of the fixing piece 74b with a predetermined gap thereamong. Both ends of the hinge axle 78 are fixed at the lower end of the plurality of hinge pieces 76. The push lever 80 is inserted and supported to the hinge axle 78 for see-saw movement.

The push lever 80 has a locking part 80a vertically bent to co-relate with the split groove 72a, and the lengthwise center of the push lever 80 is hinged at the lower end of the hinge piece 76 with the hinge axle 78. A non-slippery member is attached to the rear end of the push lever 80 for improvement of attachment force.

The elastic member 82 is made of a compressible coil spring with one end thereof fixed to the lower surface of the fixing piece 74b and the other end fixed to the upper surface of the push lever 80.

The connecting bars 90a, 90b and fixing bars 92a, 92b are coupled so that while the fixing bars horizontally slide with the corresponding connecting bars, both must revolve together in a spline coupling method.

The height level of the moving bars 98a, 98b is controlled by a control knob which is screwed in through one lower circumferential surface of the moving bars for fixing at a predetermined height level of the fixing bars 92a, 92b.

Hereinafter, the operations and effects will be described in accordance with the second embodiment of the present invention thus constructed.

Figure 4:
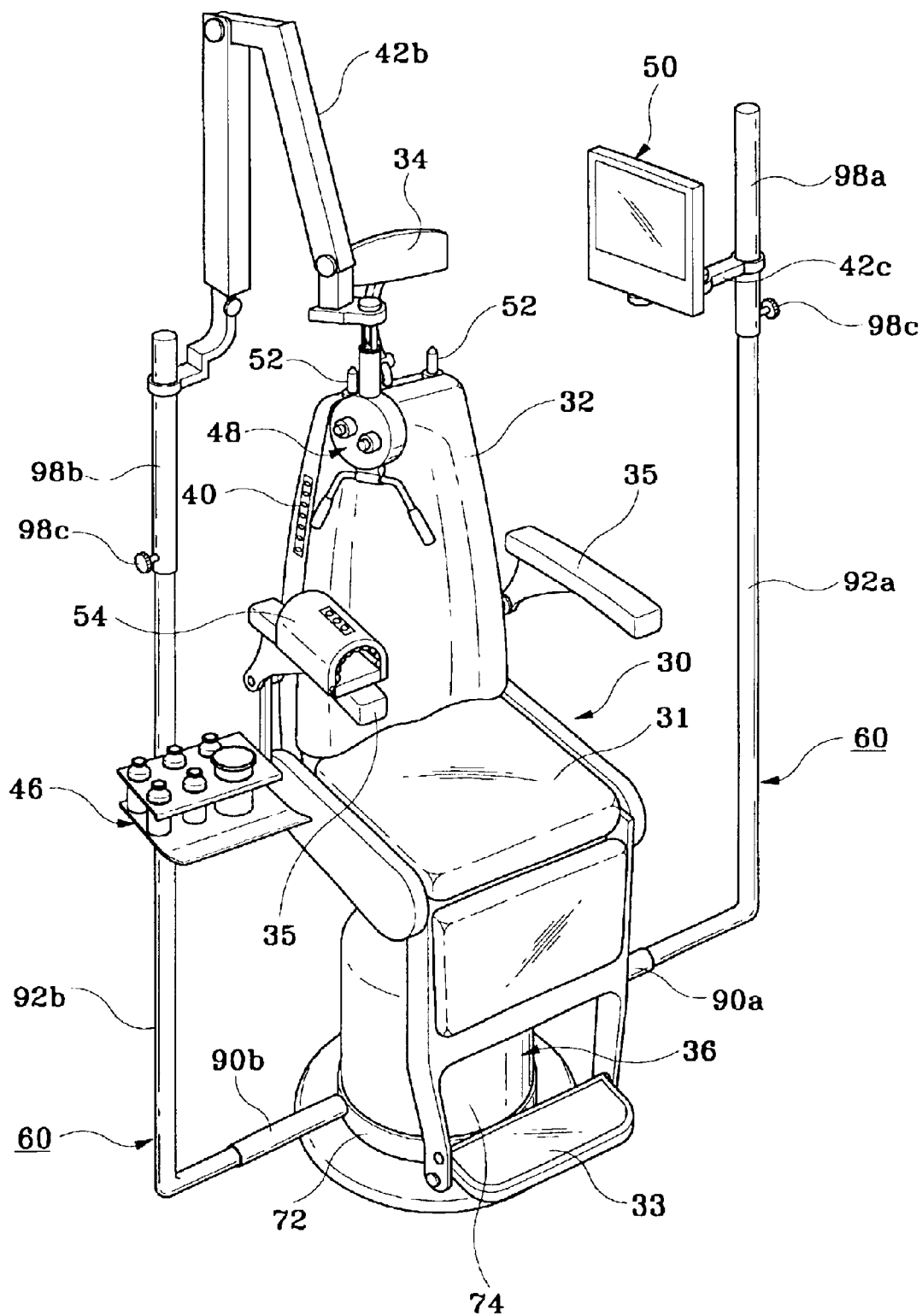
Figure 5:
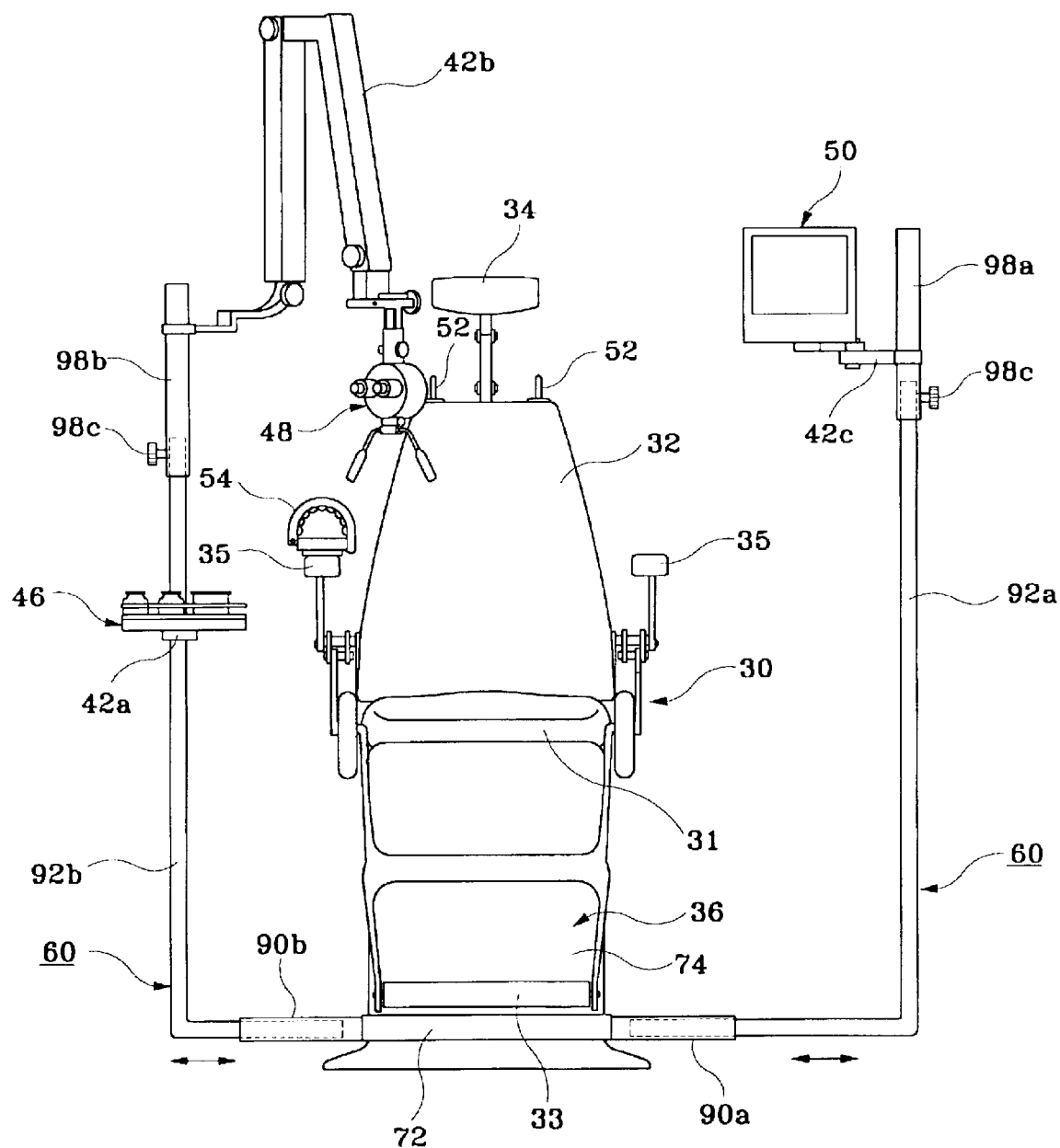

When the right ear of a patient sitting on the rotating patient chair 30 is treated, the rotational supporting means 60 is turned to control the position of the microscope 48 in correspondence with the right ear, and the position of the monitor 50 in correspondence with the left ear, as shown in FIGS. 4 and 5.

In other words, in order to get the monitor 50 and microscope 48 supported by the rotational supporting means 60 to face each other at 180 degrees in correspondence with the patient's ears sitting on the rotating patient chair 30, the practitioner steps on the push lever 80 protruded outside of the case 74. Then, the push lever 80 makes a see-saw movement around the hinge axle 78 hinged at the hinge piece 76 to enable the locking part 80a to move up. While the locking part 80a moves upwards, it gets separated from one of the split grooves 72a formed at a predetermined gap thereamong around the upper circumferential end of the rotational plate 72. Therefore, the rotational plate 72 can freely turn around the rotational axle 36a connected with the bearing 70a.

Figure 6A:
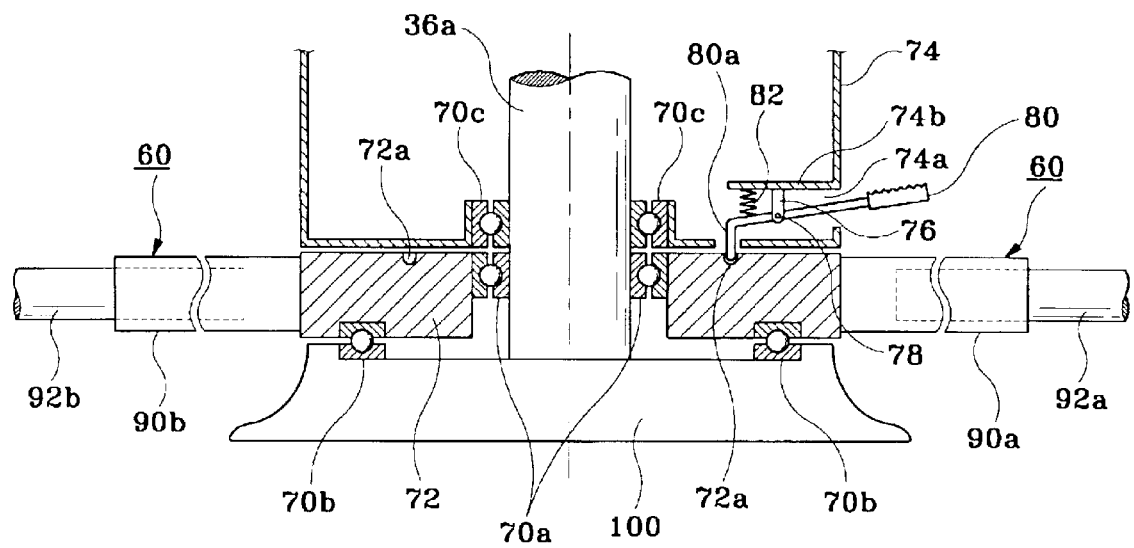
FIGS. 6a and 6b are cross-sectional views of key parts of the rotating patient chair before and after the operation of the rotational supporting means.
Figure 6B:
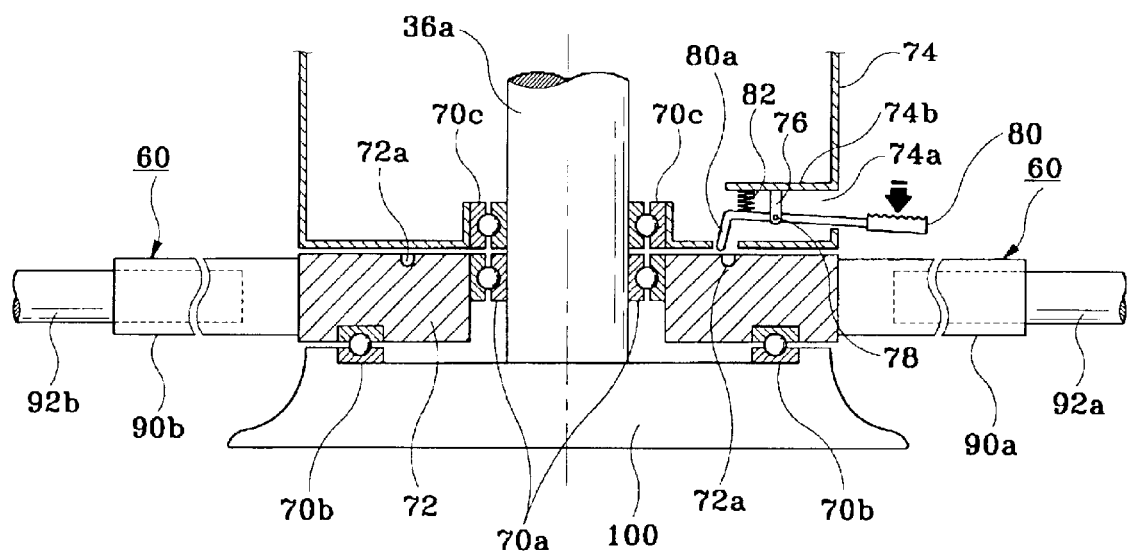

When the practitioner steps on the push lever 80, the rotational plate 72 rotates in a predetermined direction to set up the microscope 48 and monitor 50 connected to the rotational plate 72 in correspondence with the patient's ears sitting on the rotating patient chair 30. When the practitioner takes his foot off the push lever 80, the push lever 80 makes a see-saw movement arising from the elasticity of the elastic member 82 inserted between the lower portion of the fixing piece 74b of the case and the upper portion of the push lever 80 to enable the locking part 80a to move downwards for insertion into one of the split grooves 72a formed around the rotational plate 72 for fixation as shown in FIG. 6a.

Furthermore, the rotational plate 72 simultaneously rotates the connecting bars 90a, 90b fixed at both circumferential ends of the rotational plate 72. At the same time, the fixing bars 92a, 92b and moving bars 98a, 98b, respectively connected in sequence at one end of the connecting bars 90a, 90b rotate along with the monitor 50 and microscope 48 connected at the upper portions of the moving bars 98a, 98b.

Figure 7A:
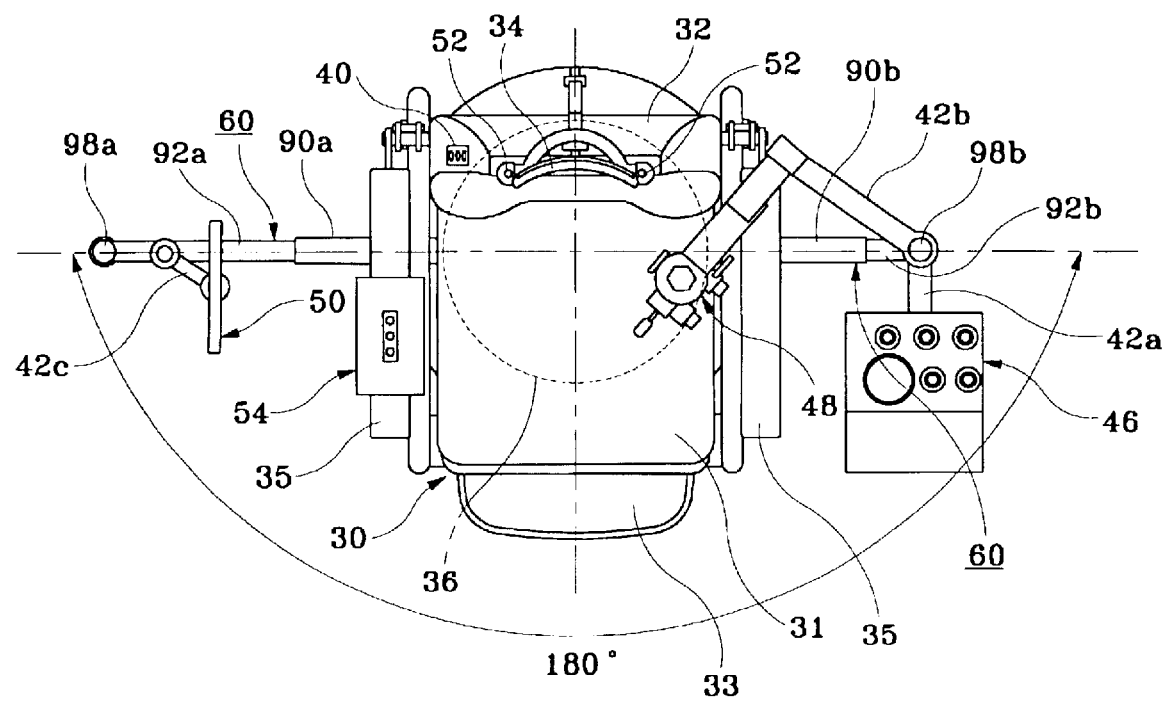
FIGS. 7a and 7b are plans for illustrating the states of the monitor and mircroscope that can simultaneously be rotated around a rotating patient chair while being maintained at 180 degrees from the center of the rotating patient chair.
Figure 7B:
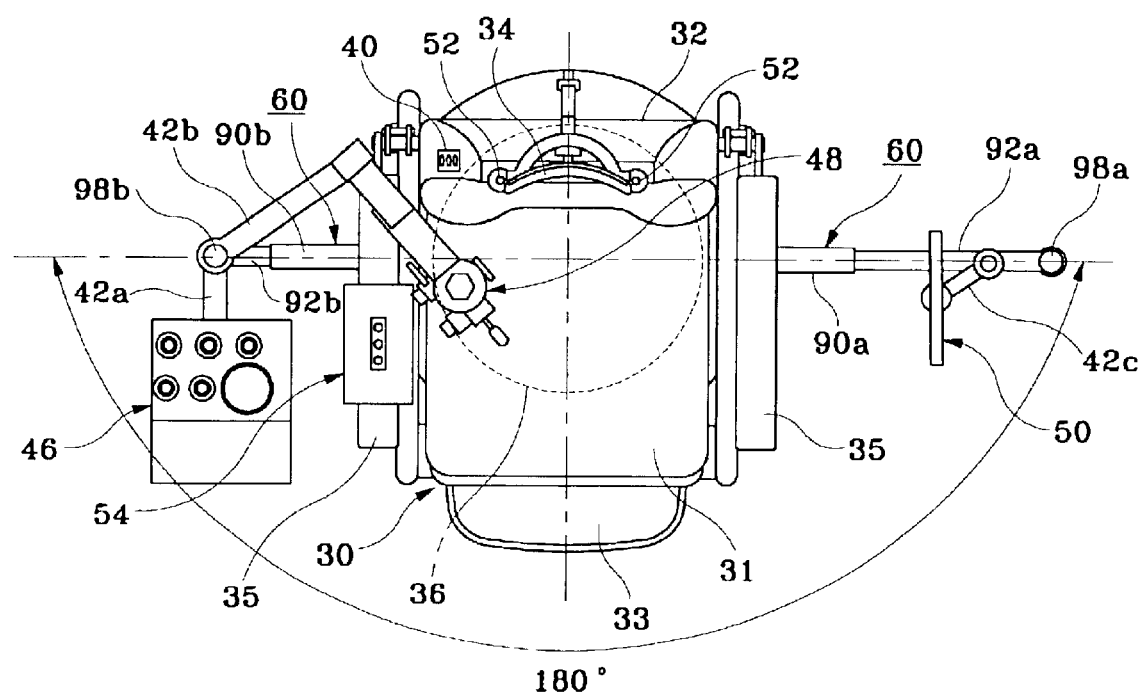

In other words, as the monitor 50 is connected to the moving bar 98a by way of the third link mechanism 42c, and the microscope 48 is connected to the moving bar 98b by way of the second link mechanism 42b, and the treatment board 46 is connected to the fixing bar 92b by way of the first link mechanism 42a, the monitor 50 connected to the moving bar 98a, opposite from the microscope 48 at 180 degrees, simultaneously rotates around the rotating patient chair 30 as desired, as shown in FIG. 7a or 7b, when the practitioner turns the moving bar 98b connected closely to the microscope 48 as desired.

Likewise, the monitor 50 and microscope 48 arranged at 180 degrees, correspondingly and simultaneously rotate around the rotating patient chair 30. When the practitioner controls the position of the microscope 48 toward one of the patient's ears while the patient is sitting on the rotating patient chair 3, the monitor 50 is turned as desired and automatically moved to a position to be aligned with the patient's sight. Thus, the patient does not need to move around, and the practitioner can treat the patient's ears while the microscope 48 is moved to the left or right side of the rotating patient chair 30.

Figure 7C:
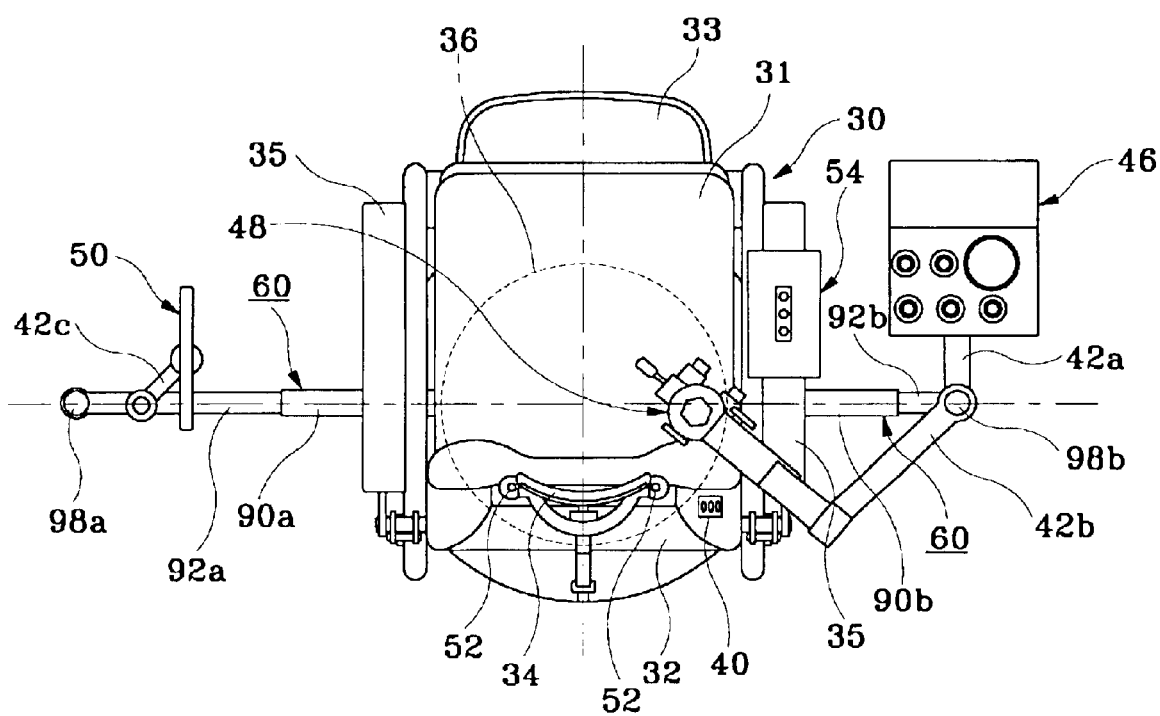
FIG. 7c illustrates the state of a rotating patient chair that can be rotated with the monitor and microscope while being maintained at 180 degrees from the center of the rotating patient chair.

Also, while the patient is seated on the designated rotating patient chair 30, the practitioner can treat the patient's ears while remaining on the practitioner's designated chair (not shown) by rotating only the rotating patient chair 30, for instance, at 180 degrees while keeping the monitor 50 and microscope 48 at the same position, as shown in FIG. 7c.

In other words, the rotational axle 36a of the rotating patient chair 30 is connected to the rotational plate 72 by way of the bearing 70a and to the case 74 by way of another bearing 70c. As the rotational plate 72 is combined with the case 74 by way of the push lever 80, the rotational plate 72 and case 74 remain constant at a predetermined angle without being rotated along with the rotational axle 36a connected with the seat 31.

Figure 8:
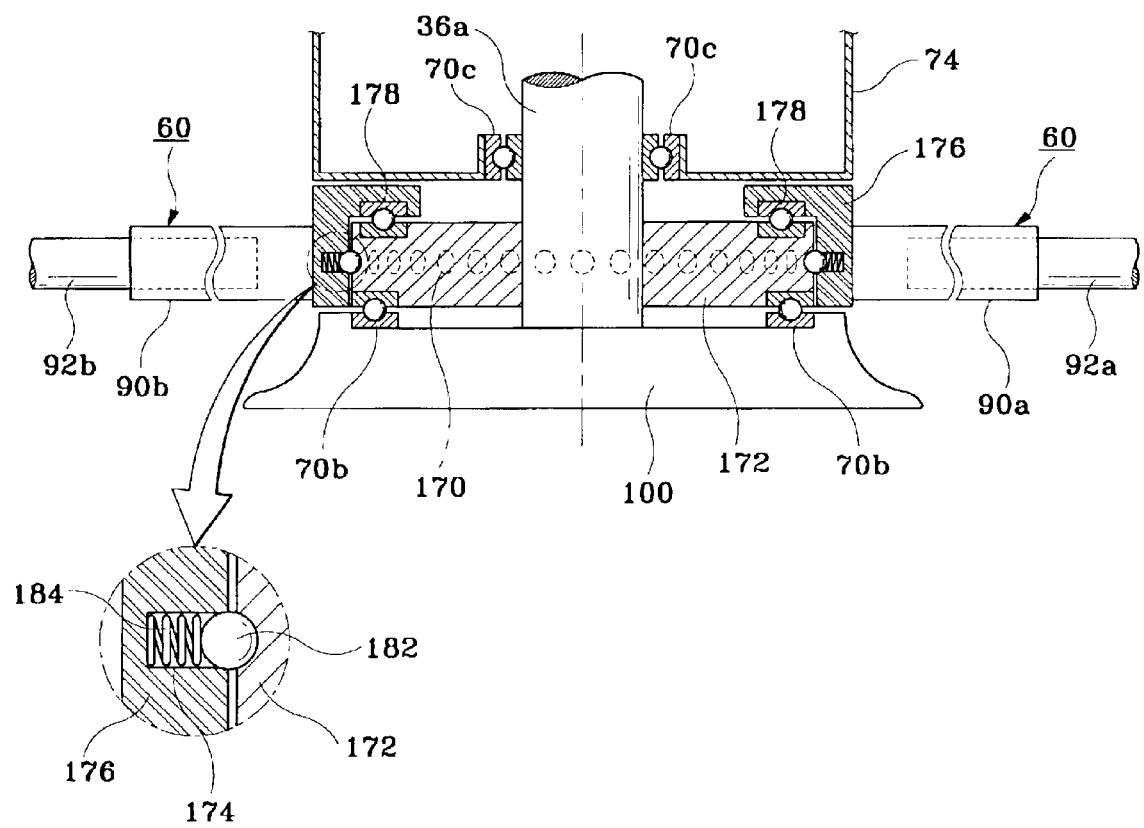
FIG. 8 is a cross-sectional view for illustrating key parts of the rotating patient chair using a lock ball at the rotational supporting means in accordance with the third embodiment of the present invention.

The third embodiment of the present invention will be described with reference to FIG. 8.

By way of reference, if the third embodiment of the present invention is identically constructed as the first and second embodiments, the same reference numerals will be used for designation of like or equivalent parts, detailed descriptions of which will be omitted.

The rotational supporting means 60 includes: a rotational plate 172 fixed on the outer circumferential surface of the rotational axle 36a for simultaneous rotation and formed at the outer circumferential surface thereof with a plurality of split grooves 170 at a predetermined gap thereamong; a rotating ring 176 oppositely arranged to the outer circumferential surface and the end portion of the upper surface at the rotational plate 172, and comprised of a plurality of recesses 174 formed in horizontal correspondence with a plurality of split grooves 170 at the internal circumferential surface thereof to rotate clockwise and counter-clockwise; a bearing 178 inserted into one horizontal side between the rotational plate 172 and rotating ring 176 to freely support the rotation of the rotating ring 176; a lock ball 182 elastically supported in the opening of the recess 174 by way of an elastic member 184 inserted into the recess 174 to slide down on the split grooves 170 for simultaneous attachment or detachment; hollow connecting bars 90a, 90b with one horizontal end thereof oppositely fixed on the outer circumferential surface of the rotating ring 176; fixing bars 92a, 92b respectively bent in the shape of an "L" figure with one end thereof inserted into the connecting bars 90a, 90b to horizontally slide down without revolving in relation to the corresponding connecting bars 90a, 90b; and moving bars 98a, 98b respectively mounted at the upper circumferential ends of the fixing bars 92a, 92b for vertical movement.

Hereinafter, the operations and effects will be described in accordance with the third embodiment of the present invention thus constructed.

In the rotational supporting means 60, when the lock ball 182 is matched with one of the split grooves 170, the lock ball 182 is inserted into and tightly contact with one of the split grooves by the elastic member 184. If the rotational force of the rotating ring 176 is greater than the elasticity of the elastic member 184, the rotating ring 176 can be rotated to a desired direction. In contrast, if the rotational force of the rotating ring 176 is smaller than the elasticity of the elastic member 184, the rotating ring 176 may not be rotated but stopped.

Figure 9A:
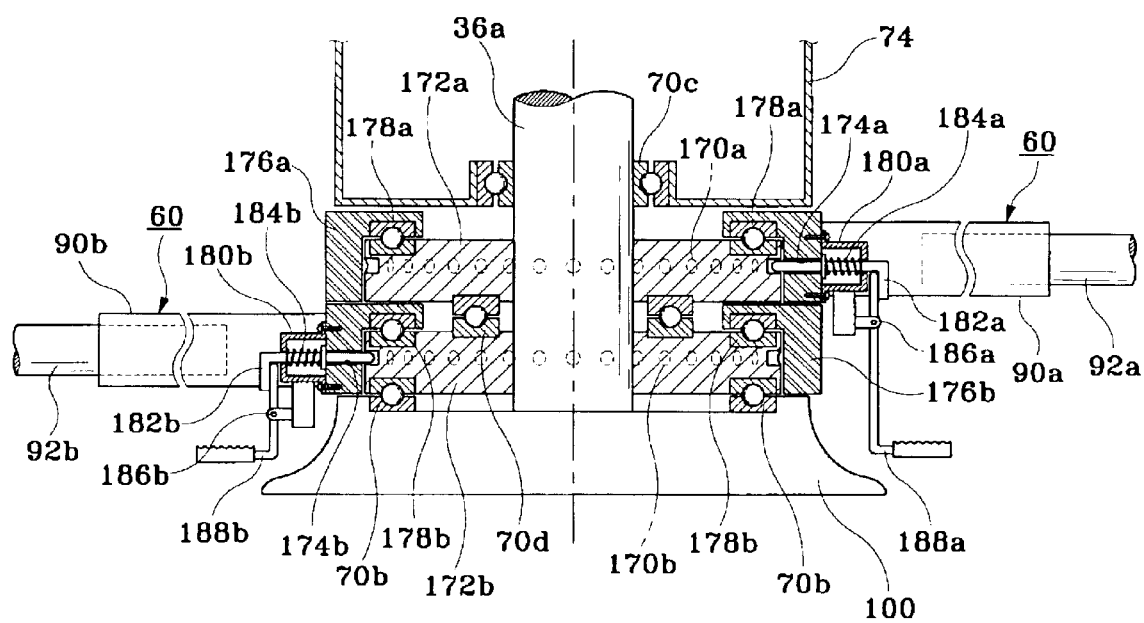

The fourth embodiment of the present invention will be described with reference to FIGS. 9a and 10.

By way of reference, if the fourth embodiment of the present invention is identically constructed as the first through third embodiments described above, identical reference numerals will be used for designation of like or equivalent parts, detailed descriptions of which will be omitted.

The rotational supporting means 60 includes: rotational plates 172a, 172b fixed on the outer circumferential surface of the rotational axle 36a for simultaneous rotation each spaced in a predetermined gap thereamong and formed with a plurality of split grooves 170a, 170b at the outer circumferential surface thereof in a predetermined gap thereamong; rotating rings 176a, 176b oppositely arranged to the outer circumferential surface and the end portion of the upper surface at the rotational plate 172a, 172b, and comprised of a plurality of through holes 174a, 174b formed in horizontal correspondence with a plurality of split grooves 170a, 170b at the internal circumferential surface thereof to rotate clockwise and counter-clockwise; bearings 178a, 178b respectively inserted into one load concentrating side between the rotational plates 172a, 172b and rotating rings 176a, 176b to separately support the rotation of the rotating rings 176a, 176b; lock pins 182a, 182b respectively and movably supported by way of fixing brackets 180a, 180b at one outer circumferential surface of the rotating rings 176a, 176b to get one end thereof selectively attached to or detached from one of the plurality of split grooves 170a, 170b in the through holes 174a, 174b; elastic members 184a, 184b installed in the fixing brackets 180a, 180b to apply elasticity to enable the lock pins 182a, 182b to respectively move forward to the outer circumferential surface of the rotational plates 172a, 172b; push levers 188a, 188b respectively hinged at the lower end of the fixing brackets 180a, 180b for vertical see-saw movement by way of hinge axles 186a, 186b and formed with an upper end hitched to the rear end of the lock pins 182a, 182b, wherein the upper end moves the lock pins 182a, 182b backward when the practitioner steps on the push levers 188a, 188b; hollow connecting bars 90a, 90b with one end thereof being respectively fixed at one horizontal circumferential surface of the rotating rings 176a, 176b; a first fixing bar 92a bent in the shape of an "L" figure with one end thereof inserted into the connecting bar 90a to horizontally slide without revolving in relation to the corresponding connecting bar 90a; a first moving bar 98a mounted at the upper circumferential surface of the fixing bar 92a for vertical movement to support the monitor 50 with the third link mechanism 42c at a predetermined upper height level; a second fixing bar 92b bent in the shape of an "L" figure with one end thereof inserted into the other connecting bar 90b for horizontal sliding without revolving in relation to the corresponding connecting bar 90b to support the treatment board 46 with the first link mechanism 42a at a predetermined height level; and a second moving bar 98b mounted at the upper circumferential surface of the fixing bar 92b for vertical movement to support the monitor 50 with the second link mechanism 42c at a predetermined upper height level.

The rotational plates 172a, 172b are integrated with the rotational axle 36a, for instance, by welding for simultaneous rotation.

The plurality of split grooves 170a, 170b of the rotational plates 172a, 172b are respectively formed, each having an identical angle around the rotational axle 36a.

The fixing brackets 180a, 180b are respectively bent in the shape of a "⊏" figure with the end thereof being fixed with a plurality of fastening bolts (reference numerals not shown), for instance, at one circumferential surface of the rotating rings 176a, 176b.

The ends of the lock pins 182a, 182b are formed in a round shape. Hitching jaws (reference numerals not shown) are respectively integrated in the lengthwise center of the circumferential surface of the lock pins 182a, 182b to place a restriction on the forward movement by being hitched at the respective through holes 174a, 174b of the rotating rings 176a, 176b. Besides, bent parts (reference numerals not shown) are respectively formed at the rear end of the lock pins 182a, 182b for convenient hitching at the upper end of the push levers 188a, 188b.

The elastic members 184a, 184b are made of compressible coil springs respectively inserted into the rear circumferential surface of the lock pins 182a, 182b. One end of the elastic members 184a, 184b is closely attached for hitching at the internal side of the fixing brackets 180a, 180b and the other end thereof is hitched at hitching jaws (reference numerals not shown) protruded at the lengthwise center of the lock pins 182a, 182b.

The push levers 188a, 188b are bent in the shape of an "L" figure to respectively form horizontal and vertical portions thereof. The center of the vertical portion is hinged by way of the hinge axle 186a, 186b at one side of the fixing brackets 180a, 180b, and a non-slippery member is attached on the surface of each horizontal portion to be used as a foot pad.

A bearing 70d is inserted between the rotational plates 172a, 172b.

Hereinafter, the operations and effects will be described in accordance with the fourth embodiment of the present invention.

Figure 9B:
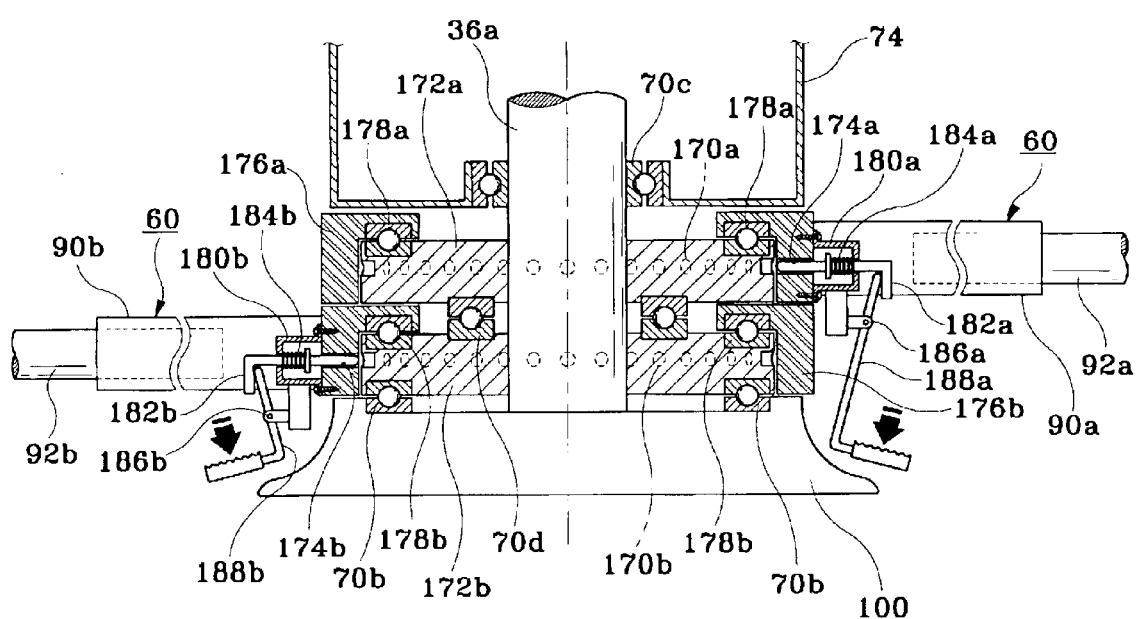

In order to control the position of the monitor 50 and microscope 48 around the rotating patient chair 30, for instance, to make them face each other by manipulation of the rotational supporting means 60, the rotational plates 172a, 172b and rotating rings 176a, 176b respectively fixed at the lower circumferential surface of the rotational axle 36a of the chair rotating drive part 36 should be placed apart, far enough to allow free rotation as shown in FIG. 9b.

The separation operation as such will be described with reference to FIG. 9b. When the practitioner steps on either of the push levers 188a, 188b protruded at the lower external end of the chair rotating drive part 36, the push levers 188a, 188b engage in a see-saw movement around the hinge axle 186a, 186b to enable the upper end thereof to rotate clockwise. At this time, the lock pins 182a, 182b respectively hitched at the upper portions of the push levers 188a, 188b horizontally move backwards by operation of the push levers 188a, 188b for separation of the ends of the lock pins 182a, 182b from the plurality of split grooves 170a, 170b formed around the circumferential surface of the rotational plates 172a, 172b and, at the same time, inserted into the through holes 174a, 174b of the rotating rings 176a, 176b. Therefore, rotational plates 172a, 172b and rotating rings 176a, 176b are separated to prevent any interference when rotational plates 172a, 172b and rotating rings 176a, 176b are rotated at different angles.

At this time, the practitioner can rotate and position the connecting bar 90a, fixing bar 92a, moving bar 98a, third link mechanism 42c and monitor 50 connected with the upper rotating ring 176a in a corresponding movement around the rotating patient chair 30 as desired.

Moreover, if the practitioner takes his or her foot off the push levers 88a, 88b after the monitor 50 and microscope 48 are properly positioned at a predetermined angle (α degrees) as desired, the lock pins 82a, 82b respectively move forward to the horizontal direction by elasticity of the elastic member 84a for selective insertion into one of the split grooves 70a, 70b each spaced in a predetermined gap thereamong relative to the circumferential surface of the rotational plates 72a, 72b. Then, the rotational plates 72a, 72b and rotating rings 76a, 76b can simultaneously be rotated along with the rotating patient chair 30.

Figure 10:
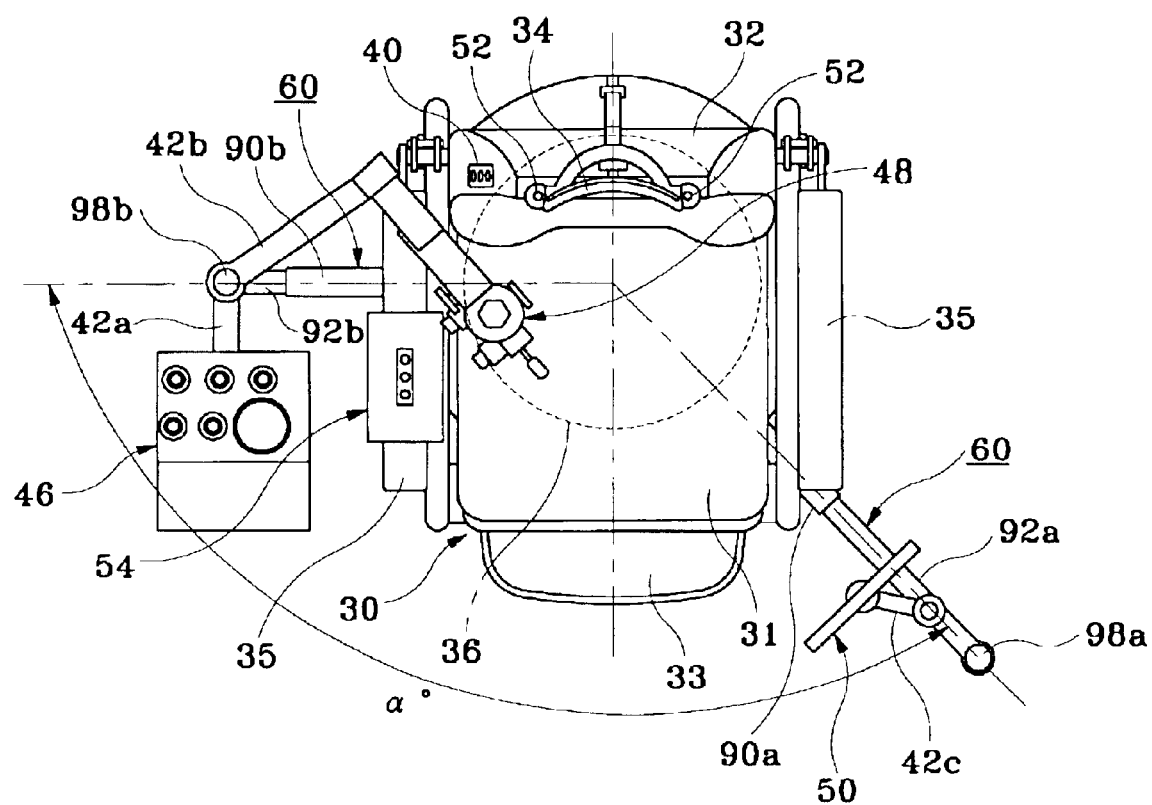

Likewise, the position of the monitor 50 and microscope 48 can be controlled by the locking operation of the lock pins 82a, 82b at a predetermined angle (α degrees) around the rotating patient chair 30 as shown in FIG. 10.

The fifth embodiment of the present invention will be described with reference to FIGS. 11 and 12.

By way of reference, if the fifth embodiment of the present invention is identically constructed as the first through fourth embodiments described above, identical reference numerals will be used for designation of like or equivalent parts, detailed descriptions of which will be omitted.

The rotational axle 36a of the chair rotating driving part 36 of the rotating patient chair 30 has a rotational supporting means 60 that completely rotates or stops around the rotating patient chair 30, and connects and supports the monitor 50 and microscope 48 to face each other along the same horizontal line.

In other words, the rotational supporting means 60 includes: a rotational plate 72 supported to the rotational axle 36a to allow free rotation around the rotating patient chair 30; a hollow connecting bar 90b horizontally fixed at the outer circumferential surface of the rotational plate 72; a fixing bar 92b bent in the shape of an "L" figure with one end thereof being inserted into the connecting bar 90b for horizontal sliding without revolving in relation to the corresponding connecting bar 90b to support the treatment board 46 with the first link mechanism 42a at a predetermined vertical height level; a moving bar 98b mounted at the upper circumferential surface of the fixing bar 92b for vertical movement to support the microscope 48 with the second link mechanism at a predetermined height level; and a supporting bar 110 mounted at the upper portion of the moving bar 98b and bent in the shape of a "┐" figure for horizontal rotation to support the monitor 50 with the third link mechanism at the horizontal end thereof.

The connecting bar 90b and the fixing bar 92b should be coupled in a spline coupling method, so that while the fixing bar 92b horizontally slides with the corresponding connecting bar 90a, both must revolve together.

The moving bar 98b is connected to control the vertical height level with a control knob 98c closely fixed in a thread-fitted manner at a predetermined height level of the outer circumferential surface of the fixing bar 92b.

The supporting bar 110 is inserted into and connected to the upper portion of the moving bar 98b with a control knob 98d to prevent vertical separation.

Hereinafter, the operations and effects will be described with reference to the fifth embodiment of the present invention thus constructed.

Figure 11:
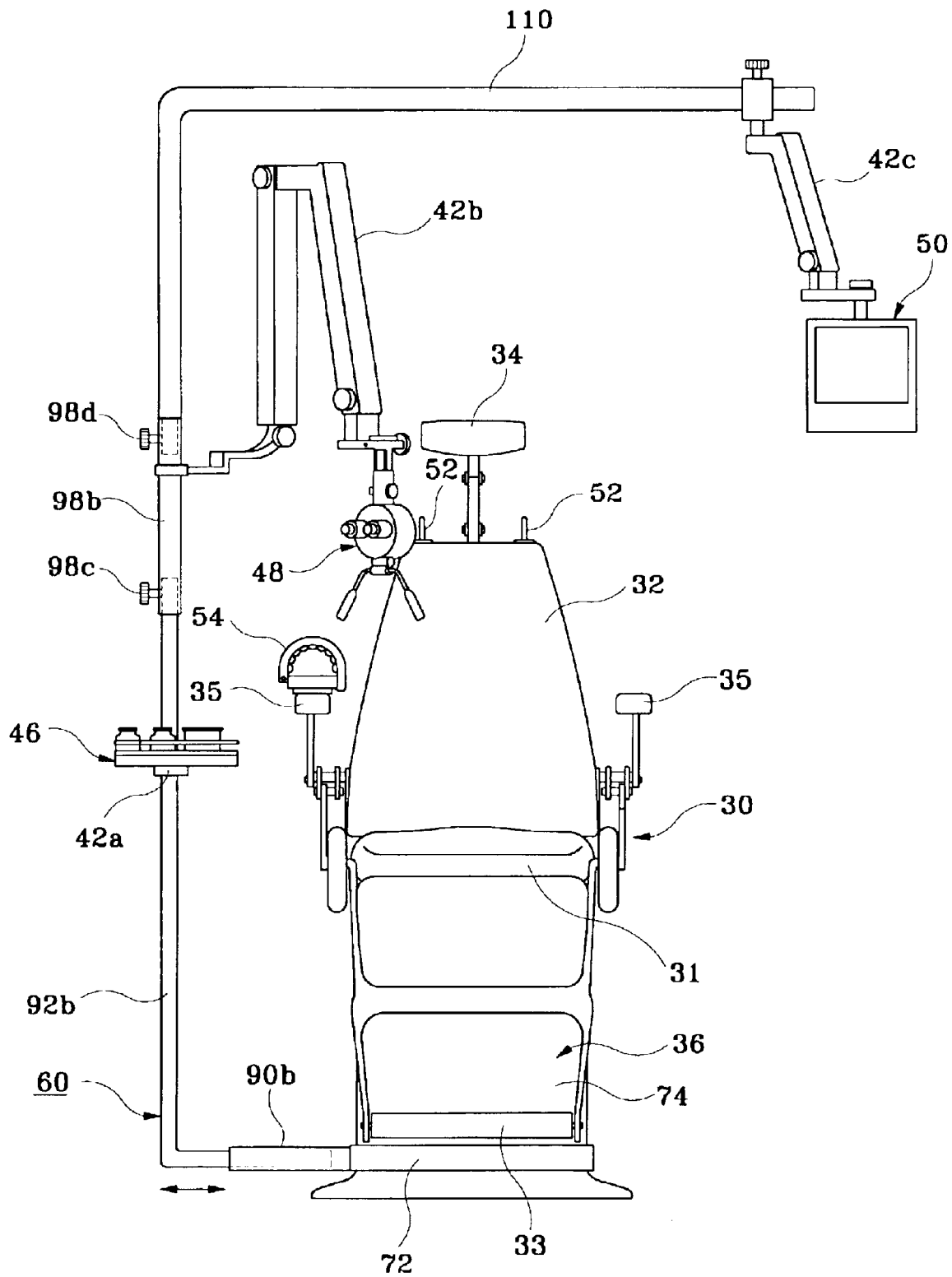
FIGS. 11 and 12 illustrate a monitor and microscope that are installed at the rotational supporting means and simultaneously rotated around the rotating patient chair in accordance with the fifth embodiment of the present invention; where
Figure 12:
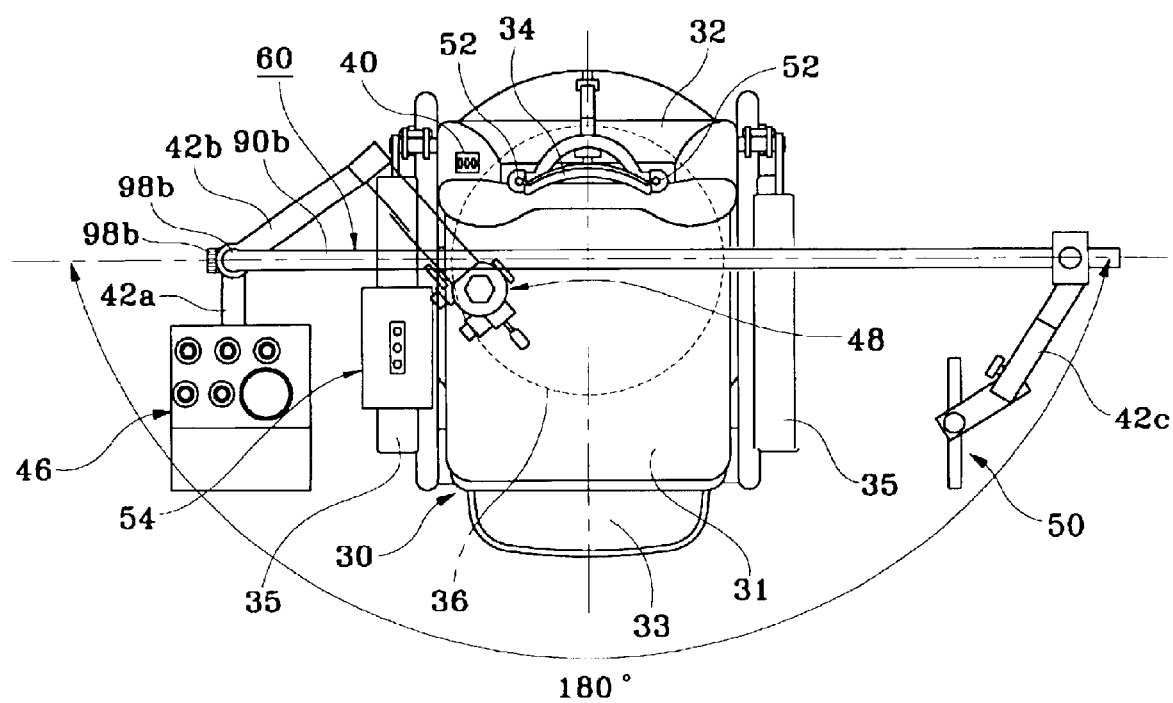

When a patient seated on the rotating patient chair 30 is treated, the rotational supporting means 60 is rotated as shown in FIGS. 11 and 12. The microscope 48 and monitor 50 simultaneously rotate around the rotating patient chair 30 synchronously with the rotation of the rotational supporting means 60 to be positioned in correspondence with both ears of the patient. For instance, when the position of the microscope 48 is controlled in correspondence with the patient's right ear, the monitor 50 is automatically positioned correspondingly.

In other words, as the rotational supporting means 60 includes the connecting bar 90b, fixing bar 92b, moving bar 98b, supporting bar 110 sequentially connected in a line, the treatment board 46 is installed at the fixing bar 92b with the first link mechanism 42a, the microscope 48 is installed at the moving bar 98b with the second link mechanism 42b, and the monitor 50 is installed at the supporting bar 110 with the third link mechanism, the treatment board 46, microscope 48 and monitor 50 all move synchronously when the rotational supporting means 60 is rotated.

Particularly, the supporting bar 110 can be turned to a predetermined angle around the moving bar 98b by releasing the control knob 98d, which fixes the lower vertical portion of the supporting bar 110 and the upper portion of the moving bar 98b. Also, the supporting bar 110 can be stopped at a predetermined height level when the control knob 98d is tightened. As a result of the aforementioned structure, the monitor 50 connected to the supporting bar 110 with the third link mechanism 42c and the microscope 48 connected to the moving bar 98b with the second link mechanism 42b can be positioned to face each other around the patient rotation chair 30.

Therefore, the supporting bar 110 illustrated in the fifth embodiment is more cost-effective effective and has a simpler structure than the second embodiment of the present invention where the microscope 48 and monitor 50 are respectively supported with the moving bars 98a, 98b.

As described above, the rotating patient chair mounted with an integrated ear diagnosis and treatment unit described in accordance with the first through fourth embodiments of the present invention is constructed with suctioners, treatment board, microscope having a camera, monitor, control box to control devices and treatment tools, so that the monitor and microscope can be positioned in correspondence with the patient's ears anatomically positioned at 180 degrees, to enable the patient to observe all of the treatment processes to his or her ear parts including the thin, dark auditory canals and eardrums, on the installed monitor and to enable the practitioner to explain all of the treatment processes shown on the monitor to the patient and his guardians, thereby improving reliability on the practitioner and the treatment processes and maximizing the treatment effects. Also, the diagnosis and treatment processes can be performed on the patient's ears by not letting the practitioner or patient move around but by merely rotating the ear diagnosis and treatment unit, thereby minimizing discomfort and inconvenience to the practitioner or patient, shortening the medical treatment time and minimizing the space of a treatment room occupied by the diagnosis and treatment unit.

The foregoing descriptions of specific embodiments of the present invention are presented for purposes of illustration and description. They are not intended to be exhaustive or to limit the invention to the precise forms disclosed. Obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A rotating patient chair mounted with an ear diagnosis and treatment unit, wherein the ear diagnosis and treatment unit includes suctioners, a treatment board, a microscope having a camera, a monitor, and the rotating patient chair includes a seat, a back rest, an arm rest, a chair rotating drive part, the chair comprising:

a first link mechanism connected with the treatment board;

a second link mechanism connected with the microscope;

a third link mechanism connected with the monitor; and a rotational supporting means that connects a rotational axle of the chair rotating drive part to the first, second and third link mechanisms and rotates around the rotational axle of the rotating patient chair to simultaneously or respectively control the position of the microscope and the monitor kept at a predetermined angle; and wherein the rotational supporting means comprises: a rotational plate supported at an outer circumferential surface of the rotational axle and rotating horizontally; a connecting bar connecting one end of the outer circumferential surface of the rotational plate to the second link mechanism; and the other connecting bar connecting the other end of the outer circumferential surface of the rotational plate to the third link mechanism.

2. The chair as defined in claim 1 further comprising a manipulating switch box mounted at one side of the back rest to control the power of the microscope, monitor and suctioners.

3. The chair as defined in claim 1, wherein the suctioners are respectfully mounted on both upper ends of the back rest.

4. The chair as defined in claim 1, wherein a blood pressure tester is mounted at an upper side of the arm rest.

5. A rotating patient chair mounted with an ear diagnosis and treatment unit, wherein the ear diagnosis and treatment unit includes suctioners, a treatment board, a microscope having a camera, a monitor, and the rotating patient chair includes a seat, a back rest, an arm rest, a chair rotating drive part, the chair comprising:

a first link mechanism connected with the treatment board;

a second link mechanism connected with the microscope;

a third link mechanism connected with the monitor; and a rotational supporting means that connects a rotational axle of the chair rotating drive part to the first, second and third link mechanisms and rotates around the rotational axle of the rotating patient chair to simultaneously or respectively control the position of the microscope and the monitor kept at a predetermined angle; wherein the rotational supporting means comprises:

a rotational plate concentrically supported via bearings at an outer circumferential surface of the rotational axle to horizontally rotate independently the rotation of the rotational axle, and circumferentially formed with a plurality of split grooves each spaced in a predetermined gap thereamong at an upper central surface thereof;

a push lever hinged via a hinge axle in an open hole formed at one side of a case of the chair rotating drive part for horizontal see-saw movement to enable a locking part at a tip end thereof to be selectively attached to or detached from one of the plurality of split grooves while a rear end thereof is protruded outside of the case;

an elastic member mounted between one side of the case and an upper end of the push lever to place an elastic force down toward the tip end of the push lever;

hollow connecting bars with one end thereof being respectively fixed at an outer circumferential surface of the rotational plate to face each other in order to rotate with the rotational plate;

a first fixing bar bent in the shape of an "L" figure with one end thereof inserted into one of the connecting bars to horizontally slide down without revolving in relation to the corresponding connecting bar;

a second moving bar mounted at an upper circumferential surface of the first fixing bar for vertical movement and to support the monitor with the third link mechanism at a predetermined height level;

a second fixing bar bent in the shape of an "L" figure with one end thereof being inserted into the other connecting bar to horizontally slide down without resolving in relation to the corresponding connecting bar, and to support the treatment board with the first link mechanism at a predetermined height level;

and a second moving bar mounted at an upper circumferential surface of the second fixing bar for vertical movement and to support the microscope with the second link mechanism at a predetermined height level.

* * * * *